# (12) United States Patent
Savage et al.

(10) Patent No.: US 7,686,800 B2
(45) Date of Patent: Mar. 30, 2010

(54) ANTI-RECOIL CATHETER

(75) Inventors: Steven Savage, Paynesville, MN (US); Greg Brucker, Minneapolis, MN (US); Douglas J. Duchon, Chanhassen, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 963 days.

(21) Appl. No.: 10/695,845

(22) Filed: Oct. 29, 2003

(65) Prior Publication Data

US 2004/0097905 A1 May 20, 2004

Related U.S. Application Data

(63) Continuation of application No. 09/479,110, filed on Jan. 7, 2000, now Pat. No. 6,669,679.

(51) Int. Cl.
*A61M 25/00* (2006.01)

(52) U.S. Cl. ........................ 604/528; 604/264

(58) Field of Classification Search .............. 604/264, 604/534, 500, 280, 96.01, 164.01, 523–532, 604/95.01–95.05
See application file for complete search history.

(56) References Cited

U.S. PATENT DOCUMENTS

| | | | |
|---|---|---|---|
| 3,731,679 A | 5/1973 | Wilhelmson et al. | |
| 3,739,943 A | 6/1973 | Wilhelmson et al. | |
| 3,828,767 A | 8/1974 | Spiroff | |
| 4,512,764 A | 4/1985 | Wunsch | |
| 4,717,381 A | 1/1988 | Papantonakos | |
| 4,769,006 A | 9/1988 | Papantonakos | |
| 4,784,638 A | 11/1988 | Ghajar et al. | |
| 4,801,297 A | 1/1989 | Mueller | |
| 4,854,324 A | 8/1989 | Hirschman et al. | |
| 4,966,579 A | 10/1990 | Polaschegg | |
| 5,037,403 A | 8/1991 | Garcia | |
| 5,078,702 A | 1/1992 | Pomeranz | ................... 604/280 |
| 5,085,635 A | 2/1992 | Cragg | |
| 5,088,991 A | 2/1992 | Weldon | |
| 5,180,364 A | 1/1993 | Ginsburg | |
| 5,207,655 A | 5/1993 | Sheridan | |
| 5,224,938 A | 7/1993 | Fenton, Jr. | |
| 5,250,034 A | 10/1993 | Appling et al. | |
| 5,254,101 A | 10/1993 | Trombley, III | |
| 5,334,154 A | 8/1994 | Samson et al. | |
| 5,380,307 A | 1/1995 | Chee et al. | |

(Continued)

FOREIGN PATENT DOCUMENTS

EP 0 025 704 A1 3/1981

(Continued)

*Primary Examiner*—Kevin C Sirmons
*Assistant Examiner*—Phillip Gray
(74) *Attorney, Agent, or Firm*—Shumaker & Sieffert, P.A.

(57) ABSTRACT

A design is disclosed for a catheter assembly used during interventional and/or diagnostic procedures. The catheter includes a plurality of openings that allow for controlled fluid flow as the fluid exits the lumen of the catheter and can be inserted into the vascular system over a guidewire. As a result, the openings balance the fluid forces and, thereby, stabilize the distal tip to accommodate a wide range of injection parameters. The particular design of the catheter assembly of the present invention also reduces and/or eliminates recoil of the catheter tip during high volume injections, such as those associated with coronary or ventricular angiography.

18 Claims, 7 Drawing Sheets

U.S. PATENT DOCUMENTS

| | | | |
|---|---|---|---|
| 5,531,679 | A | 7/1996 | Schulman et al. |
| 5,569,181 | A | 10/1996 | Heilman et al. |
| 5,584,803 | A | 12/1996 | Stevens et al. |
| 5,616,137 | A | 4/1997 | Lindsay |
| 5,643,228 | A | 7/1997 | Schucart et al. |
| 5,739,508 | A | 4/1998 | Uber, III |
| 5,795,333 | A | 8/1998 | Reilly et al. |
| 5,800,409 | A | 9/1998 | Bruce |
| 5,800,411 | A | 9/1998 | Nakada et al. |
| 5,806,519 | A | 9/1998 | Evans, III et al. |
| 5,807,349 | A | 9/1998 | Person et al. |
| 5,808,203 | A | 9/1998 | Nolan, Jr. et al. |
| 5,840,026 | A | 11/1998 | Uber, III et al. |
| 5,843,037 | A | 12/1998 | Uber, III |
| 5,843,050 | A * | 12/1998 | Jones et al. .............. 604/525 |
| 5,857,464 | A | 1/1999 | Desai |
| 5,873,861 | A | 2/1999 | Hitchins et al. |
| 5,885,216 | A | 3/1999 | Evans, III et al. |
| 5,919,171 | A | 7/1999 | Kira et al. |
| 5,920,054 | A | 7/1999 | Uber, III |
| 5,947,935 | A | 9/1999 | Rhinehart et al. |
| RE36,648 | E | 4/2000 | Uber, III et al. |
| 6,059,760 | A * | 5/2000 | Sandmore et al. .......... 604/264 |
| 6,096,011 | A | 8/2000 | Trombley, III et al. |
| 6,149,627 | A | 11/2000 | Uber, III |
| 6,197,000 | B1 | 3/2001 | Reilly et al. |
| 6,280,434 | B1 * | 8/2001 | Kinoshita et al. .......... 604/264 |
| 6,306,117 | B1 | 10/2001 | Uber, III |
| 6,317,623 | B1 | 11/2001 | Griffiths et al. |
| 6,339,718 | B1 | 1/2002 | Zatezalo et al. |
| RE37,602 | E | 3/2002 | Uber, III et al. |
| 6,385,483 | B1 | 5/2002 | Uber, III et al. |
| 6,397,098 | B1 | 5/2002 | Uber, III et al. |
| 6,402,717 | B1 | 6/2002 | Reilly et al. |
| 6,440,107 | B1 | 8/2002 | Trombley, III et al. |
| 6,442,418 | B1 | 8/2002 | Evans, III et al. |
| 6,471,674 | B1 | 10/2002 | Emig et al. |
| 6,475,192 | B1 | 11/2002 | Reilly et al. |
| 6,520,930 | B2 | 2/2003 | Critchlow et al. |
| 6,643,537 | B1 | 11/2003 | Zatezalo et al. |
| 6,652,489 | B2 | 11/2003 | Trocki et al. |
| 6,669,679 | B1 | 12/2003 | Savage et al. |
| 6,673,033 | B1 | 1/2004 | Sciulli et al. |
| 6,699,219 | B2 | 3/2004 | Emig et al. |
| 6,731,971 | B2 | 5/2004 | Evans, III et al. |
| 6,733,477 | B2 | 5/2004 | Cowan et al. |
| 6,733,478 | B2 | 5/2004 | Reilly et al. |
| 6,743,202 | B2 | 6/2004 | Hirschman et al. |
| 6,889,074 | B2 | 5/2005 | Uber, III et al. |
| 6,901,283 | B2 | 5/2005 | Evans, III et al. |
| 6,939,302 | B2 | 9/2005 | Griffiths et al. |

FOREIGN PATENT DOCUMENTS

| | | |
|---|---|---|
| EP | 0 334 640 A2 | 9/1989 |
| EP | 0 346 012 A1 | 12/1989 |
| EP | 0 362 497 A1 | 4/1990 |
| EP | 0 453 008 A1 | 10/1991 |
| EP | 0 476 796 A1 | 3/1992 |
| EP | 0 640 347 | 3/1993 |
| EP | 0 609 950 A1 | 8/1994 |
| EP | 640347 | 1/1995 |
| EP | 0 804 936 A2 | 11/1997 |
| WO | WO 94/16760 A1 | 8/1994 |
| WO | WO 96/40325 A1 | 12/1996 |
| WO | WO 97/18004 A1 | 5/1997 |
| WO | WO 98/33544 A1 | 8/1998 |

* cited by examiner

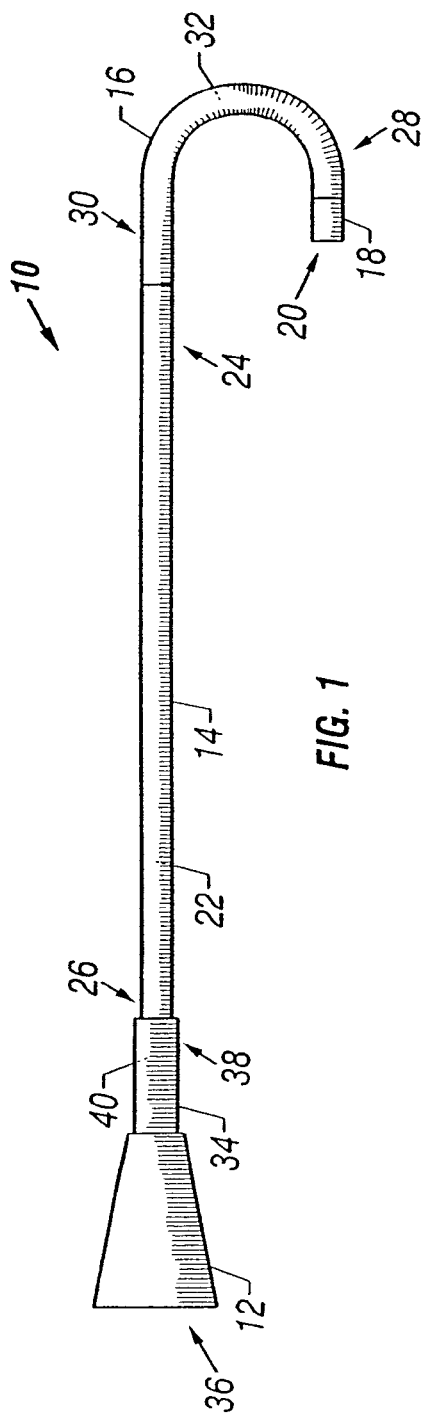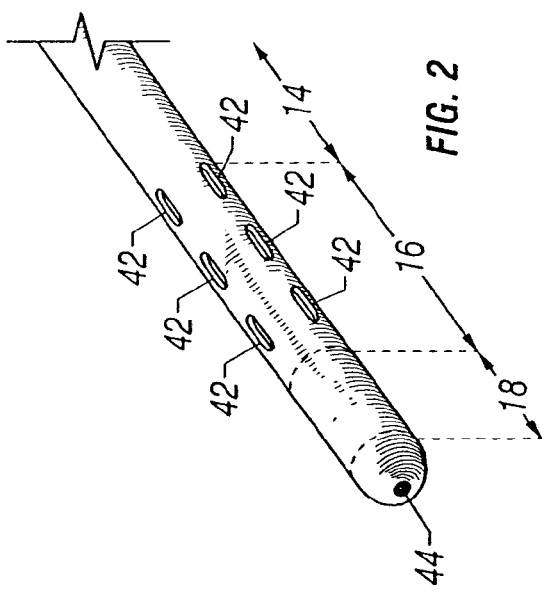

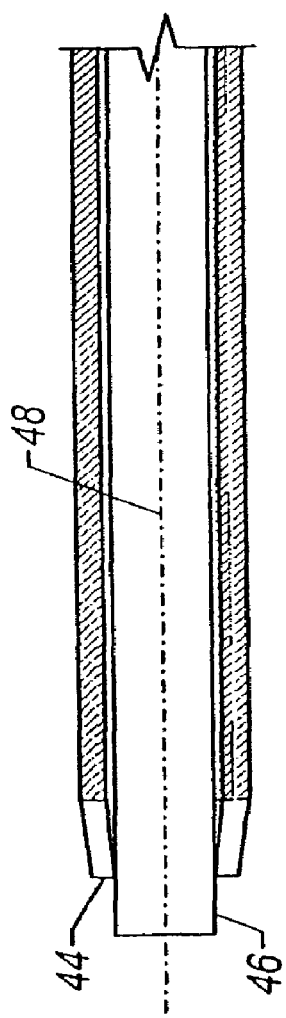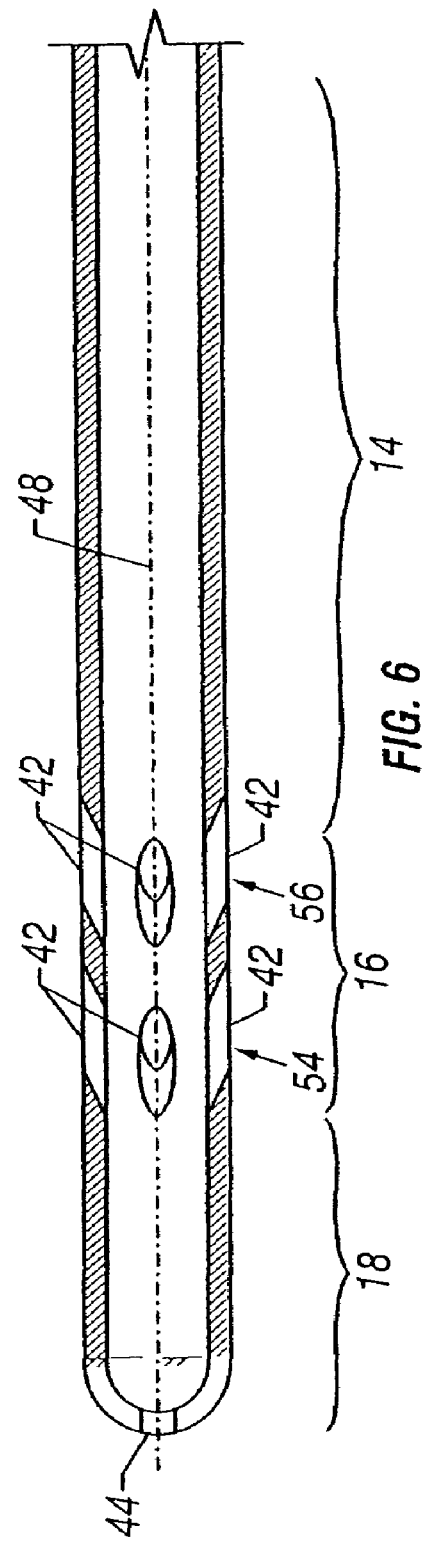

| Catheter | | Slot Configuration | | | | Restrictor | | | Flow Parameters | | Reaction | | |
|---|---|---|---|---|---|---|---|---|---|---|---|---|---|
| Test # | Diameter (Fr) | Material | Type | Geometry (mm) | # | Location (mm) | Material | Diameter (mm) | Volume (ml) | Rate (ml/sec) | Recoil Direction | Recoil Amount (mm) | Lateral Whipping (mm) |
| 1 | 4 | Hard | Angled Holes 30° | 0.254 | 8 | 1.27 3.175 | Soft | .305 | 10 | 2 | Forward | 5.08 | 5.08 |
| 2 | 4 | Hard | Angled Holes 30° | 0.254 | 8 | 1.27 3.175 | Soft | .305 | 10 | 4 | Forward | 8.89 | 3.81 |
| 3 | 4 | Hard | Angled Holes 30° | 0.254 | 8 | 1.27 3.175 | Soft | .305 | 10 | 6 | Forward | 15.24 | 15.24 |
| 4 Cordis Infinity JR 4 | 4 | Hard | No Holes | N/A | 0 | N/A | none | N/A | 10 | 4 | Backward | 111.7 Hits wall of chamber | 2.54 - 5.08 |
| 5 Cordis Sones 1 | 4 | Hard | Holes 90° | 0.685 | 2 | 5.08 7.62 | none | N/A | 10 | 4 | Backward | 111.7 Hits wall of chamber | 2.54 - 3.81 |

FIG. 12

| Catheter | | Slot Configuration | | | | Restrictor | | Flow Parameters | | Reaction (Total score of 10 divided between chambers) | |
|---|---|---|---|---|---|---|---|---|---|---|---|
| Test Position | Diameter (Fr) | Material | Type | Geometry (mm) | # | Location (mm) | Material | Diameter (mm) | Volume (ml) | Rate (ml/sec) | Downstream Chamber | Upstream Chamber |
| First | 4 | Hard | Angled Holes | 0.381 | 8 | 1.905 2.54 | Soft | 0.3302 | 10 | 8 | 4 | 6 |
| First | 4 | Hard | Angled Holes | 0.3302 | 12 | 1.905 2.54 | Soft | 0.3302 | 10 | 4 | 3 | 7 |
| Second | 4 | Hard | Angled Holes | 0.381 | 8 | 1.905 2.54 | Soft | 0.3302 | 10 | 8 | 6 | 4 |
| Second | 4 | Hard | Angled Holes | 0.3302 | 12 | 1.905 2.54 | Soft | 0.3302 | 10 | 4 | 4 | 6 |

FIG. 13

ANTI-RECOIL CATHETER

RELATED APPLICATIONS

This application is a continuation of U.S. patent application Ser. No. 09/479,110, filed Jan. 7, 2000 now U.S. Pat. No. 6,669,679.

FIELD OF THE INVENTION

The present invention relates to catheters used during interventional and/or diagnostic procedures for delivering fluids into a patient. The present invention particularly relates to an angiographic catheter having controlled fluid flow properties for delivering fluids, such as contrast media, into a human or animal body.

BACKGROUND OF THE INVENTION

Catheters are commonly used in the diagnosis and treatment of various medical conditions and advancements in catheter designs and materials have made them particularly well-suited for intravascular procedures and intravascular therapies. A conventional catheter includes a small, elongated tube made of flexible, biocompatible materials that enable the catheter to be easily maneuvered through body passages and vascular structures. During an angiographic procedure, the distal end of the catheter is typically inserted into the body via small incisions in the groin area or upper arm and guided through anatomical passages and/or blood vessels to a target site using guide wires and associated imaging techniques. The proximal end is then connected to the device for performing the desired procedure. One such device is an angiographic injector such as the injector disclosed in U.S. patent application Ser. No. 08/957,228 and/or the injector disclosed in U.S. Pat. No. 5,800,397, both of which are commonly assigned to the owner of the present application and both of which are hereby incorporated by reference.

An example of a procedure using a catheter is angiography. Angiography is a procedure used to specifically image, diagnose and treat abnormalities in the heart or vascular structures. During angiography, a physician inserts a catheter and injects contrast material through the catheter into a vein or artery of a patient. The area of the patient's body injected with the contrast material is imaged using x-ray energy or magnetic fields (as used in magnetic resonance imaging) and the resulting image is recorded and/or displayed on a monitor. The images can be used for many purposes, including diagnostic activities as well as interventional procedures such as angioplasty, wherein a balloon is inserted into a vascular system and inflated to open a stenosis.

During the injection procedure, fluid typically flows out of the open distal end of the catheter tip. However, the fluid dynamics associated with some catheter designs often cause the catheter to be pushed back or to recoil as a result of the velocity of the fluid as it exits the distal tip. In effect, the recoil force of the catheter is directly proportional to the fluid velocity at the tip.

Such undesirable recoil movement is particularly acute when using a catheter of small size, e.g. less than about 4 French, since these catheters experience particularly high fluid exit velocities due to the flow requirements in a typical angiographic procedure. However, even larger catheters may be prone to higher recoil if fluid flow out of the tip is of sufficient velocity. Overall, however, smaller angiographic catheters are more prone to severe whipping and recoil at the outset of an injection than catheters of a larger size. This, in part, is due to the structural characteristics of the catheters. In particular, as catheter shaft diameter decreases, the bending force is reduced by the diameter to the third power. Thus, a reduction in shaft diameter from 6 to 4 French gives a four fold reduction in bending force given the same load and distance at which the load is applied.

Catheter designs incorporating valves or openings located along the distal portion of the catheter wall have been considered in an attempt to better facilitate control of the fluid flow. An example of such a device may be found in U.S. Pat. No. 5,250,034, which discloses a pressure responsive valve catheter. The catheter is formed of a relatively non-compliant material, such as nylon, to prevent the sidewalls of the catheter from expanding under the high internal fluid pressures. Slits formed in the catheter wall act as pressure responsive valves to permit fluid to exit the internal lumen of the catheter while preventing material from entering the catheter lumen via the slits. The catheter also includes a distal end hole which may be sealed with an occluding ball located on a guide wire, thereby causing all the fluid to flow from the slits. Alternatively, when the occluding ball is not seated in the end hole, both the fluid and guide-wire may exit from the end hole.

Another example may be found in U.S. Pat. No. 5,807,349, which discloses a catheter having a valve mechanism to permit the infusion or aspiration of fluids between the catheter and the vessel in which the catheter is positioned. The valve is located at the distal end of the catheter and, preferably, is in a plane which is oriented at an angle to the longitudinal axis of the catheter.

The above-described catheters used during angiographic procedures (and other similar devices not specifically described) offer many advantages to control fluid flow. However, it has been discovered that these catheter designs do not adequately address problems with catheter recoil within the vessel or body cavity. Further, these and other state of the art catheter valve mechanisms may still suffer from erratic opening and closing of the valves which can trigger catheter recoil. Furthermore, none of these designs nor any other designs known to the inventors appear to address the particularly acute problem of recoil with small (e.g. less than about 4 French) catheters used in angiography procedures.

In this connection, it is also important to note that there is a continuing need and desire in the medical field to reduce trauma to patients that are undergoing invasive therapies. In the context of catheter placement, this desire has led to a consideration of how to reduce patient trauma during the placement and removal of the interventional catheter.

In current techniques, the catheters that are used require a sizable incision in the patient such that there is considerable pain encountered by the patient and considerable attention to wound control is demanded of the clinician. Indeed, the wound created for such procedures requires the clinician to apply a sizable bandage or other wound containment device (e.g., a product known as Perclose from Percutaneous Vascular Surgery) in order to ensure proper treatment and closure of the wound. Furthermore, such a wound requires significant time in order for proper healing to occur.

As a result, there is an increasing desire to use smaller sized catheters in such interventional therapies so as to make the intervention as minimally invasive as possible. Such small catheters require a significantly smaller incision and thus trauma is reduced and quicker healing is obtained. However, as stated previously, such smaller catheters typically are accompanied with drawbacks such as undesirable flow characteristics (e.g. recoil).

In view of the above, although presently available catheters seem well accepted by the medical community and generally function as required, it is desirable to have a catheter with more controlled fluid flow characteristics and less invasive attributes. In particular, it is desirable to have a small diameter catheter that allows for the management of fluid forces to stabilize the distal tip over a wide range of injection parameters. It is also desirable that there be substantially low or no recoil of the catheter tip in a small diameter catheter during high volume injections, such as those associated with coronary or ventricular angiography. In addition, it is desirable to have a "universal" catheter that may be used for a variety of surgical procedures and that reduces trauma inflicted on the patient. The concept of a "universal" catheter, as applied to the present invention, is similar to a muzzle brake device that attaches to the outside barrel of any firearm and functions to reduce recoil of the firearm while maintaining discharge accuracy. Therefore, as with the muzzle brake device, it is desirable that the present invention is adaptable to a variety of catheter designs and reduces catheter movement during various medical procedures.

OBJECTS AND SUMMARY OF THE INVENTION

In view of the foregoing, it is an object of the present invention to provide a catheter assembly that addresses the obstacles and disadvantages associated with the current problem of catheter recoil caused by undesirable fluid forces during an injection procedure.

A further object of the present invention is to provide a small diameter catheter assembly that allows for the management of fluid forces to stabilize the distal tip over a wide range of injection parameters.

A further object of the present invention is to provide a catheter that is less invasive and reduces patient trauma.

These and other objects not specifically enumerated herein are believed to be addressed by the present invention which contemplates a catheter assembly comprising a hub section located at a proximal end of the catheter, a shaft section attached to the distal end of the hub, a stem section that is connected to the distal end of the shaft, and a distal tip section attached to the distal end of the stem section. In addition, the catheter assembly also includes a plurality of openings located in the stem and tip sections that provide proper balancing of fluid forces as the fluid exits the openings of the catheter.

A further object of the present invention is to provide a catheter for use in performing a medical procedure comprising an elongated tubular structure having a proximal end and a distal end. The tubular structure is configured to be a size of no greater than about 4 French and is designed to accommodate fluid flow rates in a range of approximately 0 to 40 ml/sec, and pressures up to 1200 psi, without causing failure of the tubular structure. In addition, the distal end of the catheter includes an elastic restrictor and a plurality of openings arranged such that forces resulting from the fluid flow are substantially balanced during performance of the medical procedure. The elastic restrictor is also configured to allow insertion of a guidewire greater than 0.508 mm in diameter through the distal end of the restrictor.

A further object of the present invention is to provide a method of performing a medical procedure by providing a catheter having a proximal end and a distal end and having a size no greater than about 4 French and introducing the catheter into a patient. The procedure also involves introducing a fluid into the patient at a flow rate in the range of approximately 0 to 40 ml/sec without causing failure to the catheter. Since the flow rate is limited to the maximum pressure allowed based on catheter size, a 4 French catheter will allow for a flow rate of 15 ml/sec maximum at 1200 psi. A final objective of the method includes balancing forces acting on the catheter resulting from the introduction of fluid flow by variably restricting the fluid flow at the distal end of the catheter according to the flow rate and by directing fluid out of a plurality of openings in a wall of the catheter.

A further object of the present invention is to provide a fixture for measuring catheter movement during a simulated injection procedure. The fixture comprises a plurality of walls forming at least one chamber. A first wall of the fixture includes one or more openings sized to hold a catheter. The fixture also includes a second wall including a grid such that catheter movement can be calculated and scaled against the grid.

A further object of the present invention is to provide a method of measuring catheter movement during a simulated injection procedure. The method includes filling a chamber of a test fixture with fluid and suspending a catheter from the fixture. The method also includes flowing an amount of a fluid at a controlled flow rate through the catheter and measuring catheter movement against a grid on the test fixture.

A further object of the present invention is to provide a fixture for measuring fluid backflow from a catheter during a simulated injection procedure. The fixture comprises a plurality of walls forming a first chamber and a second chamber, wherein the first chamber and the second chamber are filled with a fluid. The fixture also includes a first wall having one or more openings sized to hold a catheter and a second wall separating the first chamber and the second chamber. The second wall includes an opening such that an amount of dyed fluid flowing from the catheter into the first chamber and the second chamber can be measured based on a visual comparison and rating of dye density between the first chamber and the second chamber.

A further object of the present invention is to provide a method of measuring fluid backflow from a catheter during a simulated injection procedure. The method includes filling a first chamber and a second chamber of a test fixture with fluid and suspending a catheter from the fixture. Further, the method includes positioning the catheter in an opening of a wall separating the first chamber from the second chamber and flowing an amount of a dyed fluid at a controlled flow rate through the catheter. The amount of fluid backflow is then determined by visually comparing and rating dye density between the first chamber and the second chamber.

BRIEF DESCRIPTION OF THE DRAWINGS

Other features and advantages of the present invention will be seen as the following description of particular embodiments progresses in conjunction with the drawings, in which:

FIG. 1 is a side perspective view of a catheter assembly in accordance with the present invention;

FIG. 2 is a perspective view of a portion of a catheter assembly in accordance with the present invention;

FIG. 5 is a cross-sectional view of a guidewire inserted into a catheter assembly in accordance with the present invention;

FIG. 6 is a cross-sectional view of a catheter assembly in accordance with the present invention;

FIG. 12 is a chart illustrating catheter movement as tested on a catheter assembly in accordance with the present invention; and FIG. 13 is a chart illustrating fluid backflow as tested on a catheter assembly in accordance with the present invention

DETAILED DESCRIPTION OF THE INVENTION

Figure 3:
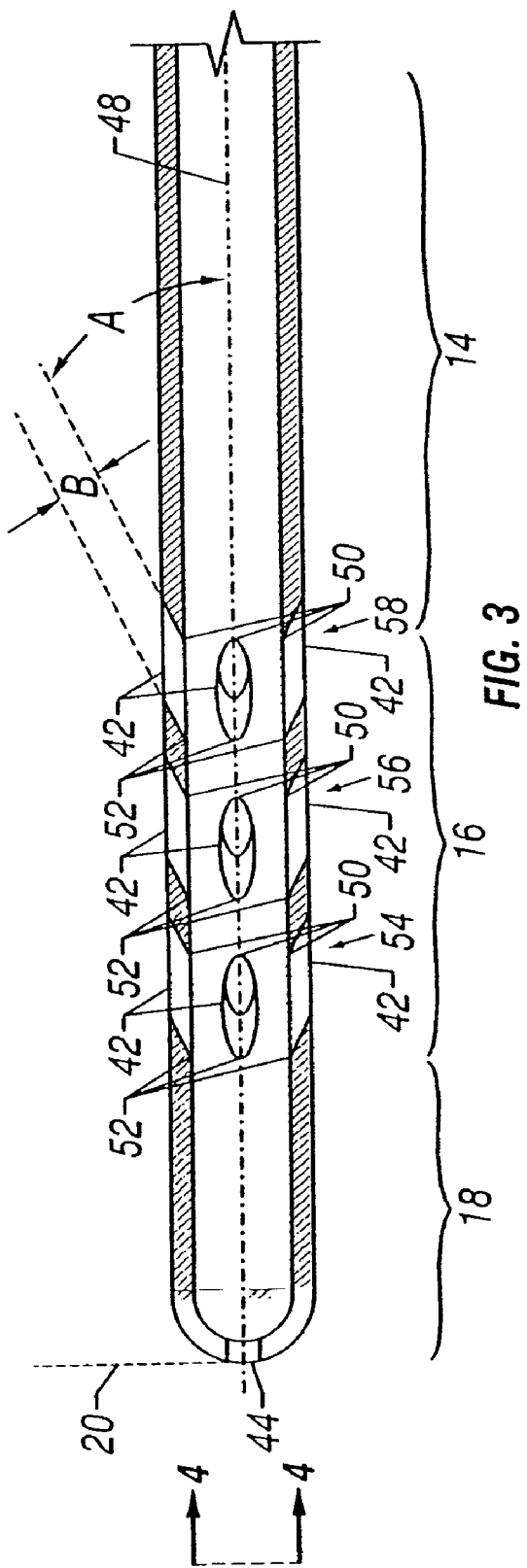
FIG. 3 is a cross-sectional view of a catheter assembly in accordance with the present invention.

Referring to FIG. 1, an embodiment of a conventional catheter 10, such as a diagnostic catheter used during angiography or other procedures, in accordance with the present invention includes four major sections including a hub 12, shaft 14, stem 16 and tip 18. The entire length of the catheter assembly 10, including the four major sections, has a maximum external or outside diameter of approximately 4 French. As discussed in greater detail below, the tip configuration in combination with the small size of the catheter diameter results in a catheter having improved management of fluid forces that better stabilize the distal tip 20 of the catheter 10 over a wide range of injection parameters.

As shown in FIG. 1, the majority of the catheter 10 comprises the shaft portion 14 which includes a central lumen 22, a distal end 24 and a proximal end 26. The through lumen 22 of the shaft 14 communicates with the tip 18 for passage of devices or fluids. Attached to the proximal end 26 of the shaft 14 is the hub 12. The hub 12 provides a standard interface for syringes, injectors, and other similar devices and affords access to the central lumen 22 of the shaft 14. The stem section 16 of the catheter assembly includes a distal end 28 and a proximal end 30. The proximal end 30 of the stem section 16 is attached to the distal end 24 of the shaft 14 and includes a central lumen 32 connected to the shaft lumen 22. Located at the distal end 28 of the stem 16 is the catheter tip 18.

In one embodiment of the present invention, the hub 12 is frustro-conically shaped with an associated cylindrical portion 34 located at the smaller diameter, distal end of the hub. Other appropriate hub 12 geometries, such as tubular, frustrospherical, funnel-shaped, or the like, may also be used with the device of the present invention. In general, however, the overall hub design is such to allow the hub to be compatible with standard luer specifications.

The proximal end 36 of the hub 12 has a preferred inner diameter of approximately 4.2 mm. However, the proximal diameter 36 of the hub 12 can range from 1.0 to 4.2 mm, or any suitable size that enables a syringe or similar device to fit into the hub 12 of the catheter 16. In a preferred embodiment, the distal end 38 of the hub 12 has an inner diameter in the range of 0.9 to 1.1 mm, forming a hub lumen 40 that cooperatively mates with the lumen 22 of the catheter shaft 14.

As shown in FIG. 1, the catheter assembly 10 further includes a shaft 14 that extends along the longitudinal axis of the catheter. The inner diameter/lumen 22 of the shaft 14 has a manufacturing specification of 1.0±0.05 mm. In a preferred embodiment, the shaft 14 comprises a multi-layered tube having a first, inner plastic layer extruded from a polymeric material, such as Pebax® (manufactured by Autochem) having a durometer of approximately 50-60 D. Other polymer materials such as urethane or nylon based may also be used, provided that these materials have a shore hardness in the range of approximately 50-60 D durometer.

The second layer of the shaft 14 comprises a metallic or polymer based material, such as stainless steel braiding, carbon fibers, extruded polymer tubing or similar materials having various configurations capable of withstanding pressures resulting from torque or other manipulations of the shaft, that is applied by a conventional manufacturing process and covers the first polymeric material layer. Alternatively, the shaft 14 may also be fabricated from plastics having radiopaque fillers, usually chemical salts of bismuth or barium or elements such as platinum or tungsten. The second layer circumscribes and extends along the shaft 14 to provide sufficient rigidity and structural support to the catheter 10. The third or outer layer comprises a polymeric material similar to that of the first layer and is extruded, or applied by other suitable means, over the braided layer. The material configuration of the shaft 14 provides structural strength and enhances rotational stiffness for placement of the catheter 10 at the target site.

Referring to FIG. 1, the stem section 16 of the catheter 10 comprises a solid plastic tube with a central lumen 32 that mates or connects to the distal end 24 of the shaft lumen 22. The stem 16 and shaft 14 are bonded together via heat-bonding, welding or other similar processes. In a preferred embodiment of the invention, the stem 16 section has a manufacturing specification of 1.0±0.05 mm for its inner diameter and 25.0±2.0 mm for its longitudinal length. The particular length of the stem section 16 of the catheter 10 may vary depending upon the type of procedure to be performed, user technique, patient parameters and the like.

The stem section 16 is made of a material that is softer than the shaft 14 material. In a preferred embodiment, the stem 16 material is made of approximately 40-50 D durometer Pebax® material loaded with a radiopaque material. Such radiopaque materials include chemical salts of barium or bismuth or pure elements such as platinum or tungsten or other similar materials. Such radiopaque materials may be incorporated into the stem section, attached or embedded into the stem section in a wire or ring configuration. The softer material of the stem 16 section, together with its particular geometric shape, enables the stem section 16 to conform to the area of the vessel or body organ that is being catheterized.

As shown in FIG. 1, the distal tip section 18 of the catheter 10 is attached to the distal end 28 of the stem section 16. In a preferred embodiment, the tip section 18 is approximately 3.0±1.0 mm in length and has a full-spherical radius of curvature, similar to a bull-nose shape. Preferably, the bull-nosed tip 18 is made of approximately 30-40 D durometer Pebax® loaded with a radiopaque material. Such radiopaque materials include chemical salts of barium or bismuth or pure elements such as platinum or tungsten or other similar materials. Such radiopaque materials may be incorporated into the stem section, attached or embedded into the stem section in a wire or ring configuration. The preferred material is Pebax® loaded with bismuth trioxide because of its biocompatability, mechanical properties and superior radioopacity characteristics.

Alternatively, the tip section 18 may be comprised of various other materials, such as a soft plastic, provided that the material characteristics are such so as to reduce injury and trauma to the inside of the organ or vasculature as the catheter 10 is moved through the system. In general, the material of the tip section 18 should be sufficiently elastic to allow for expansion to accommodate guidewires having outside diameters that are larger than the internal lumen of the restrictor. Further, the material of the tip section 18 should also allow for expansion of the restrictor in response to increased fluid pressure during an injection procedure.

In a preferred embodiment of the invention, the catheter size is small, in the range of about 4 French. In normal procedures, such small catheters are required to enable practical flow rates of up to 15 ml/sec. along with the requisite pressure variations without failure in the catheter structure. As such, the catheter materials must contain proper strength in order to accommodate these operation parameters.

Additional structural features of the stem 16 and tip 18 sections of the catheter assembly of the present invention are shown in FIGS. 2 and 3. One or more openings 42, such as holes, slits, slots, valves or other similar types of cavities, are formed in the wall of the stem section 16 near the distal end 20 of the catheter 10. The openings 42 form a conduit(s) in the wall of the stem section 16 that interconnects the internal lumen of the catheter 10 to the outside surface of the catheter body. As such, fluid flowing through the internal lumen of the catheter 10 can easily exit the catheter 10 via the conduit(s).

In a preferred embodiment of the present invention, best illustrated in FIG. 3, the openings 42 of the stem section 16 are angled toward the proximal 36 or hub 12 end of the catheter 10. This particular angle configuration causes the fluid exiting the internal lumen of the catheter 10 to flow in a retrograde direction to the fluid stream. Consequently, the resulting direction and magnitude of the fluid flow as it exits the catheter 10 supplies forces urging the catheter 10 in a forward or distal direction. Further, by properly spacing the openings 42 along the stem section 16 of the catheter 10, the lateral or radial forces generated by the rearward motion of the fluid as it exits the catheter 10 are ideally balanced. As a result, the stem section 16 configuration of the present invention substantially reduces or all-together prevents a recoil, whipping motion or excessive movement of the tip 18 during an injection.

Figure 4:
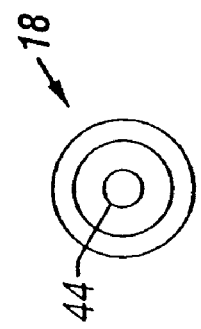
FIG. 4 is a cross-sectional end view of a catheter assembly in accordance with the present invention.

Referring to FIGS. 2, 3 and 4, the soft material of the tip section 18 is also constructed to include a small opening or restrictor 44 located at the distal end 20 of the tip 18. In a preferred embodiment, the diameter of the restrictor 44 is approximately 0.305±0.05 mm. Alternatively, the restrictor 44 may be any structure or design feature formed in or attached to the catheter 10. The particular placement and shape/design of the restrictor 44 may vary provided that its overall configuration causes resistance to fluid flow in the forward direction, thereby forcing the fluid to flow through the openings located along the stem section 16 of the catheter body and allowing for good pressure measurement.

As shown in FIG. 5, the restrictor 44 is also designed to allow passage of a guidewire 46 through the distal end 20 of the tip 18 via expansion and elastic deformation of the tip material. When the guidewire 46 is inserted through the restrictor 44 of the tip section 18, any significant amounts of fluid flow through the tip 18 are restricted and re-directed through the openings 42 of the stem section 16. However, when using a smaller guidewire, such as an angioplasty guidewire having a diameter of approximately 0.254-0.356 mm, fluid flow through the tip 18 may increase.

Typically, during use of the device, however, fluid is not introduced in the internal lumen of the catheter 10 when the guidewire 46 is positioned in the tip 18 since the purpose of the guidewire 46 is to guide or steer the catheter 10 to the target site and not function as a flow inhibitor. After the catheter 10 is positioned in the body, fluid is then injected into the lumen of the catheter 10 for delivery to the target site.

Alternatively, when the guidewire 46 is removed from the catheter 10, fluid flows through the openings 42 of the stem section 16 and the restrictor 44 of the tip section 18. The small size of the restrictor 44 and elasticity of the tip section 18 function to provide a controlled amount of fluid flow out of the distal end 20 of the tip 18. The elasticity of the tip 18 allows for a variable fluid force restriction which is proportional to the fluid flow rate. For example, as fluid flow increases, the size of the opening of the restrictor 44 also increases. As such, there is a relatively linear relationship between fluid flow and restrictor 44 size, similar to the elastic response of a spring.

In one embodiment, the flexibility of the tip section 18 may be selected such that the restrictor 44 diameter increases in size under certain flow conditions. In a preferred embodiment, the tip section 18 has a durometer of about 30-40 D and a restrictor 44 size of about 0.305±0.05. It appears that this combination is effective at obtaining the desired expansion of the restrictor 44 under normal ranges of operating flow rates. For typical procedures, such as a coronary procedure, the flow rate in a small catheter (e.g. less than 4 French) is less than approximately 20 ml. Such a flow range often leads to maximum pressures of approximately 1200 psi in such small catheters.

By redirecting fluid flow from the restrictor 44 to the openings 42 of the catheter 10 of the present invention, the rearward force exerted on the catheter shaft 14 is substantially reduced. In particular, the forces generated by fluid flowing out of the angled openings 42 located along the stem section 16 counteract the rearward, recoil forces created by the fluid flowing out of the restrictor 44. As such, the particular configuration of the openings 42 together with the unique design of the restrictor 44 appears to provide a substantial cancellation of the fluid force vectors, thereby preventing excessive, undesirable movement of the catheter 10.

The catheter 10 of the present invention also offers many safety features and advantages. For example, the openings 42 of the stem section 16 reduce or eliminate the occurrence of jet lesions at the distal end 20 of the catheter 10. This feature not only prevents possible trauma to vessel structures and tissue due to the fluid forces, but also minimizes the potential of vessel wall stains when contrast material is used during an injection procedure.

In addition, the openings 42 located along the catheter body also act as pressure relief valves when the distal tip 18 of the catheter 10 inadvertently abuts the wall of a vessel. As such, the fluid forces are redistributed and allowed to flow out through the openings 42 so that the injection procedure can safely continue. Further, the pressure relief feature of the present invention also allows an operator of the device to continue to obtain accurate pressure measurements when one of more openings 42, 44 of the catheter are obstructed without having to terminate the procedure. As a result, the device of the present invention also enhances user convenience.

Figure 7:
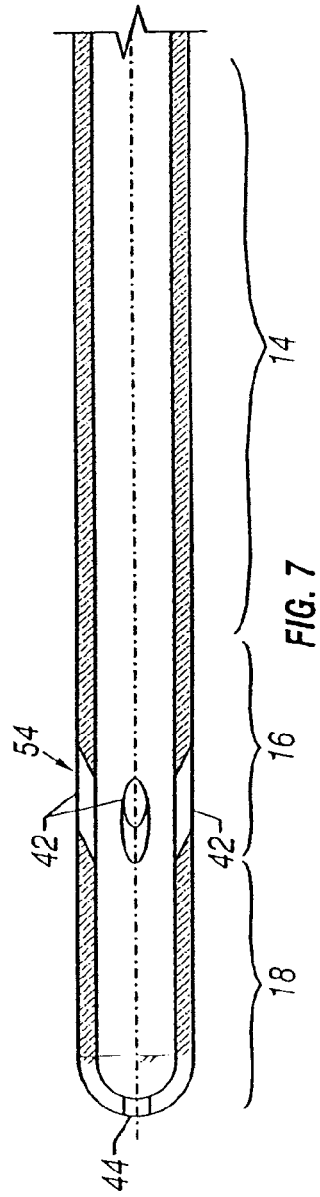
FIG. 7 is a cross-sectional view of a catheter assembly in accordance with the present invention.

Several embodiments of the device of the present invention illustrating the dimensions, quantity and placement of the openings 42 along the stem section 16 of the catheter 10 are shown in FIGS. 3, 6 and 7. As shown in FIG. 3, the catheter assembly includes a total of twelve openings 42 that are equally spaced in three rows of four openings along the longitudinal axis 48 of the stem section 16. Each opening 42 is approximately 0.3302 mm in diameter and comprises a proximal end 50 and a distal end 52. In one embodiment of the present invention, the angle A of each opening 42 is approximately 30° (+0°, −5°) from the longitudinal axis 48 of the catheter body and is formed toward the proximal 36 or hub 12 end of the catheter 10. Alternatively, the angle A of each opening 42 may range from approximately 10° to 50°, based upon desired fluid flow characteristics and catheter type.

The openings 42 are manufactured via a punching process, however other manufacturing methods may also be used. The angled/elongated or elliptical appearance of the openings 42 results from a circular opening being punched or formed in an angled plane. As such, if one were to view the openings 42 in true position, i.e. perpendicular to the plane of the openings 42, the openings would appear to be circular in shape.

Referring to FIG. 3, the first row 54 of openings 42 includes four, circumferentially spaced conduits that are located approximately 4.24±0.2 mm from the distal end 20 of the tip 18 to the distal end 52 of each opening 42. Likewise, the proximal ends 50 of the second row 56 of openings 42 are located approximately 5.76±0.2 mm from the distal end 52 of each opening 42 in the first row 54. Further, the third row 58 of openings 42 are spaced approximately 7.79±0.2 mm from their proximal ends 50 to the distal end 52 of each opening 42 in the first row. This particular longitudinal spacing and circumferential alignment of openings 42 in the stem section 16 in combination with the restrictor 44 design in the tip 18 provides for proper balancing of the flow forces generated by fluid flow, thereby substantially eliminating the occurrence of distal tip 18 movement, such as recoil, when used in the coronary artery, or lateral motion, when used in the ventricle or aorta.

In a preferred embodiment of the present invention, a total of eight openings 42 are located in the stem section 16 of the catheter 10. As shown in FIG. 6, the spacing and alignment of the openings 42 in this embodiment of the invention are similar to that of the previous embodiment except that the third row 58 of openings 42 has been removed. In yet another embodiment, shown in FIG. 7, both the second 56 and third row 58 of openings 42 have been removed, thereby leaving a total of four equally spaced openings 42 in the stem section 16 of the catheter 10.

Figure 8A:
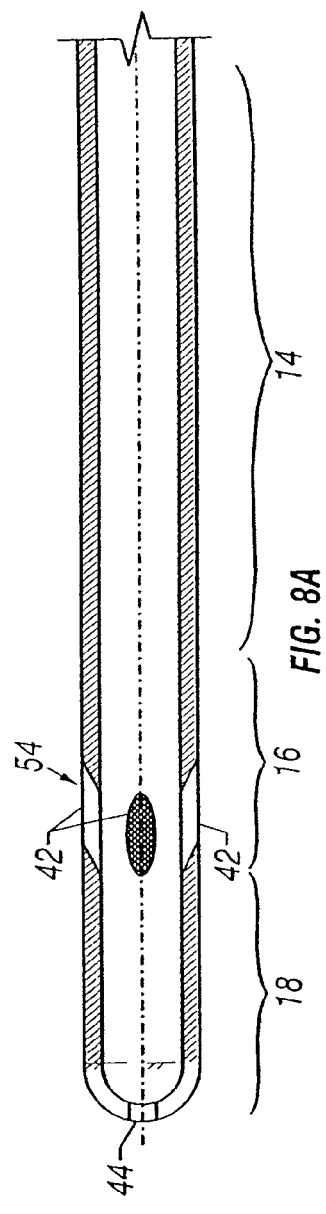
FIG. 8*a* is a perspective view of a catheter assembly in accordance with the present invention.
Figure 8B:
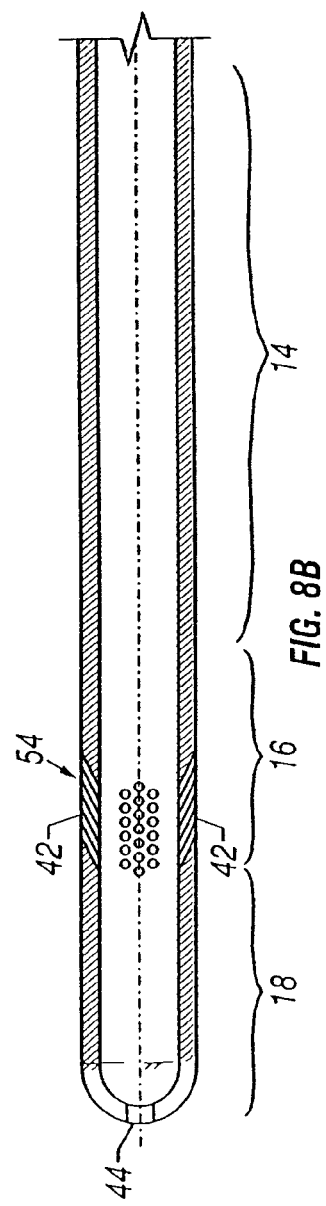
FIG. 8*b* is a perspective view of a catheter assembly in accordance with the present invention.

The catheter of the present invention may include various numbers and configurations or shapes of openings 42, 44. In one embodiment, the catheter may also include a diffuser that diffuses fluid flow through the openings 42. As shown in FIGS. 8a and 8b, the diffuser may be a screen positioned over the openings 42 or, alternatively, may be a series of small holes or openings that, cumulatively, form an opening 42. However, the location, size, and quantity of openings 42, 44 must be such that the fluid flow forces are substantially balanced, thereby causing a net fluid flow force of zero.

Although the catheter 10 of the present invention has been described to include four major sections, it is to be understood that this device also includes less than four and/or more than four sections. For example, the catheter 10 may be comprised of a single section having various material, design and structural characteristics along its length. The specific material, design and structural characteristics of the catheter 10 are individually configured to accommodate the medical environment in which the catheter 10 is to be used. Therefore, when used during an ventricular angiography procedure, the catheter 10 would likely include several sections and a pigtail shaped end with a series of openings. In contrast, when used during a coronary angiography procedure, the catheter 10 would comprise several sections and have a specific distal end shape, such as a judkins left.

Alternatively, the catheter 10 may be constructed so that each row of openings is located on a separate section of the catheter 10. Further, the catheter 10 may also comprise additional sections having unique material, design or structural characteristics specifically tailored to accommodate the particular procedures to be performed with the device of the present invention.

As such, it should be understood that the invention is not limited to the embodiments disclosed above. In particular, with respect to the quantity, size and placement of openings 42 in the stem 16 and tip sections 18 of the catheter 10, the design characteristics of the openings 42 include those embodiments that provide proper balancing of the distal and side forces created by the forward and rearward motion, respectively, of the fluid as it flows out from the internal lumen and exits the openings 42 of the catheter body. Therefore, the catheter 10 of the present invention is not limited to the specific examples or configurations previously disclosed, but may also include variations of these embodiments and still remain within the spirit of the invention.

Test Fixtures and Methods

Various types of angiography procedures were simulated using several embodiments of the present invention. The tests were specifically designed to simulate an injection procedure and determine the effects of fluid flow forces on catheter movement during an injection procedure. In addition, the test results were also used to evaluate the various catheter design parameters including, but not limited to, quantity of openings, configuration of tip restrictor, and diameter of the openings. Due to the sensitivity of the tests and significant environmental and mechanical differences between and in vivo injection procedure and a simulated injection procedure, the results obtained from the simulation represent a worst-case scenario of fluid flow effects on catheter movement. However, the data from these tests are extremely valuable since they highlight the importance of properly balancing catheter parameters in order to substantially reduce or eliminate recoil and/or whipping motions of the catheter body during injection procedures.

Figure 9:
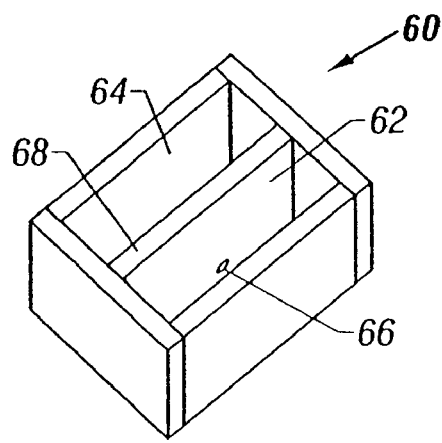
FIG. 9 is a perspective view of a test fixture for a catheter assembly in accordance with the present invention.

Specially designed test fixtures and test procedures were created to simulate a typical angiography injection and measure catheter movement during the injection procedure. As shown in FIG. 9, one test fixture 60 consists of a transparent or semi-transparent box, such as one made of acrylic, having at least two chambers 62, 64. Both chambers are filled with water or a similar fluid to approximate the internal area and pressures of a body or vascular structure. It is preferred that the test fixture 60, or at least a portion of the test fixture 60, is transparent and filled with a virtually transparent fluid to allow an operator of the device to view fluid flow in the fixture 60 during an injection procedure.

Figure 10:
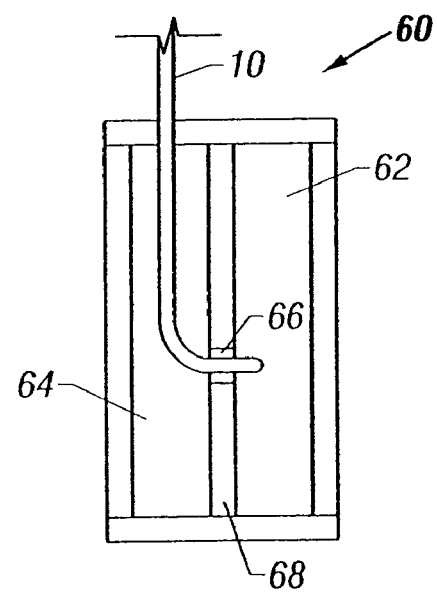
FIG. 10 is a cross-sectional view of a test fixture for a catheter assembly in accordance with the present invention.

As shown in FIG. 10, a through-hole 66 centrally located near the bottom half of a separator wall 68 is sized to simulate the ostium of a vascular structure through which the catheter 10 is to be inserted. The distance between the top 68 of the test fixture and the location of the through-hole 66 represents a worst-case scenario of catheter placement in a vascular structure. Typically, when used on a human subject, various lengths or sections of the catheter 10 are supported by surrounding tissue structures, thereby limiting catheter movement. In contrast, when used on the test fixture 60 of the present invention as shown in FIG. 10, the catheter 10 is suspended in an unsupported manner from the top 68 of the fixture 60. As a result, the effects of fluid flow on catheter movement are more pronounced using the test fixture 60 of the present invention.

To determine the amount of backflow generated by fluid flowing out of the openings 42, 44 of the catheter 10, the catheter 10 is tested at two positions in the test fixture 60. In a first position, the distal end 20 of the catheter tip 18 is contained in the through-hole 66 of the separator wall 68. A dyed fluid is injected at a specified flow rate into the proximal end 36 of the catheter 10 simulating an angiographic injection procedure. The force of the dyed fluid flowing out of the restrictor 44 and openings 42 and impinging on the walls of the through-hole 66 causes some of the dyed fluid to flow back from the first chamber 62 into the second chamber 64. A visual comparison of dye density between the first and second chambers 62, 64 is made using a ten point scoring scale. For example, a first chamber 62 score of nine and a second chamber 64 score of one indicates relatively little fluid backflow, compared to a first chamber 62 score of two and a second chamber 64 score of eight.

To further evaluate the effects of fluid backflow, the catheter 10 is also tested in a second position whereby the distal end 20 of the catheter tip 18 extends beyond the through-hole 66 of the separator wall 68. When the catheter 10 is situated in the second position, the restrictor 44 is fully contained in the first chamber 64 of the test fixture 60. As a result, only the fluid flow forces generated by the dyed fluid flowing out of the openings 42 of the catheter 10 and impinging on the walls of the through-hole 66 cause some of the dyed fluid to flow back into the second chamber 64. As before, a visual comparison and rating of dye density between the first and second chambers 62, 64 of the test fixture 60 are made using a ten point scoring scale.

Figure 11:
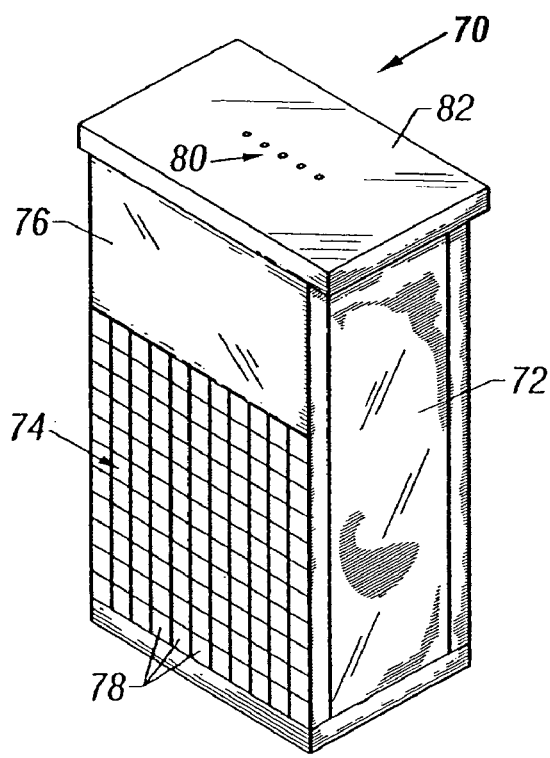
FIG. 11 is a perspective view of a test fixture for a catheter assembly in accordance with the present invention.

A second test fixture 70 used to evaluate the amount of catheter movement caused by fluid flow during an injection procedure is shown in FIG. 11. The second test fixture 70 comprises a transparent or semi-transparent box, such as one made of acrylic, having at least one chamber 72. As with the first test fixture 60, the chamber 72 of the second test fixture 70 is filled with water or a similar fluid to approximate the internal area and pressures of a body or vascular structure. It is preferred that the test fixture 70, or at least a portion of the test fixture 70, is transparent and filled with a virtually transparent fluid to allow an operator of the device to view catheter movement in the fixture 70 during an injection procedure.

As shown in FIG. 10, a grid pattern 74 is located on a front wall 76 of the test fixture 70. The size of each square 78 of the grid 74 is approximately 5 mm×5 mm, although other square sizes may also be used depending on the type of test procedure to be performed and the desired test measurement accuracy. The grid pattern 74 is used as a scale to measure catheter movement during an injection procedure simulation.

During use of the test fixture 70, a catheter 10 is held or suspended from one of several holes 80, located on the top wall 82 of the test fixture 70, so that the distal tip 18 of the catheter 10 is positioned in the area of the grid pattern 74. If the tip section 18 of the catheter 10 is curved, both recoil and lateral movement of the catheter 10 can be measured using the test fixture 70 of the present invention. For example, positioning the catheter 10 so that its tip section 18 is in a plane parallel to the grid pattern 74 allows an operator to measure catheter recoil. In addition, lateral movement of the catheter 10 can be similarly measured by simply rotating the catheter 10 90° along its longitudinal axis so that its tip section 18 is relatively perpendicular to the grid pattern 74 of the test fixture 70.

To measure catheter recoil, a fluid is injected at a specified flow rate into the proximal end 36 of the catheter 10 simulating an angiographic injection procedure. As the fluid flows out of the restrictor 44 and openings 42 of the catheter 10, an operator measures the amount of catheter movement due to fluid flow forces using the grid pattern 74 of the test fixture 70. It should be noted that the same procedure may also be used to measure lateral movement of the catheter 10, provided that the catheter 10 is properly positioned in the test fixture 70.

Test Results

Tests were conducted using the above described test fixtures 60, 70 and prototypes of the device of the present invention. As shown in FIG. 12, the tests utilized two prototype catheters 10 of the present invention. One catheter 10 design included eight angled openings 42 located along the stem section 16 and a restrictor formed in the distal tip section 18. The other catheter 10 design included twelve angled openings and a restrictor. The 90° through-hole of each opening 42 comprised a diameter of approximately 0.33 mm. Similarly, the diameter of the restrictor 44 was approximately 0.305 mm.

During the first set of experiments, 10 ml of fluid were injected at a flow rate of approximately 2 ml/sec into the catheter 10 having eight angled openings. As shown in FIG. 11, during the first experiment, there was a forward recoil of approximately 5.08 mm and a lateral movement of approximately 5.08 mm.

During the second and third tests of the experiment, 10 ml of fluid were also injected into the catheter 10. However, for this particular set of experiments, the fluid flow rate was increased to approximately 4 ml/sec and 6 ml/sec, respectively. As shown in FIG. 12, the amount of catheter recoil and whipping motion under these experimental conditions was also minimal, ranging from 3.81 mm to 15.24 mm.

Similar tests were also performed on conventional catheters. One of the conventional catheters did not include openings along its stem portion, whereas the other conventional catheter included two, non-angled openings along its stem section. As shown in FIG. 12, the amount of lateral movement due to fluid flow forces for the conventional catheters was similar to that of the present invention. However, the amount of recoil was dramatically greater for the conventional catheters compared to the catheter of the present invention.

Therefore, as shown in FIG. 12, the data on the prototypes of the present invention confirms that the quantity, size and arrangement of openings 42, 44 in the stem 16 and tip 18 sections substantially influence fluid flow forces. As such, proper balancing of catheter parameters can substantially reduce or eliminate recoil and/or whipping motions of the catheter body during injection procedures.

A second set of experiments testing fluid backflow was also performed on the catheters 10 of the present invention. As shown in FIG. 13, 10 ml of fluid were injected into the catheters 10 at flow rates which varied from 4 ml/sec to 8 ml/sec. Each catheter 10 was tested at two positions in the test fixture 60. In the first position, the distal end 20 of the catheter tip 18 was contained in the through-hole 66 of the separator wall 68 of the test fixture 60. In the second position, the distal end 20 of the catheter tip 18 extended beyond the through-hole 66 of the separator wall 68.

In general, the catheter 10 having twelve angled holes generated less fluid backflow than the catheter 10 having eight angled holes. In addition, as shown in FIG. 12, there appeared to be a lesser amount of dyed fluid in the downstream chamber when the catheter tip 18 was contained in the through-hole 66 of the separator wall 68, as opposed to extending beyond the wall 68.

Therefore, as with catheter recoil and lateral movement, the arrangement and configuration of openings 42, 44 in the stem 16 and tip 18 sections substantially influence fluid backflow. Further, as shown in FIG. 12, fluid flow rate and catheter tip 18 placement in the injection site also have an effect on fluid backflow for the catheter 10 of the present invention.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A catheter for use in performing a medical procedure comprising:

an elongated tubular structure having a proximal end and a distal end;

said tubular structure having an external diameter of no greater than about 4 French; and said distal end of said tubular structure having, on an end of a tip section, an elastic restrictor that, when operable, changes in size in response to a change in fluid flow through said tubular structure to provide a variable amount of fluid force restriction as fluid flows through said elastic restrictor, said distal end of said tubular structure further having, on a sidewall of said tubular structure, a plurality of openings, wherein at least one of said openings is formed on said sidewall at an acute angle with respect to a longitudinal axis of said distal end of said tubular structure that contains said sidewall, and wherein said openings are arranged such that forces resulting from fluid flow out of said openings and from fluid flow out of said elastic restrictor are substantially balanced in both axial and radial directions, with respect to said longitudinal axis of said distal end of said tubular structure, during performance of said medical procedure.

2. The catheter of claim 1, wherein said restrictor comprises a diameter of approximately 0.305 mm.

3. A catheter assembly comprising:

a hub section located at a proximal end of said catheter assembly;

a shaft section attached to a distal end of said hub;

a stem section connected to a distal end of said shaft, said stem section comprising one or more openings formed on a sidewall of said stem section, wherein at least one of said openings is formed on said sidewall at an acute angle with respect to a longitudinal axis of a portion of said stem section containing said sidewall; and a distal tip section attached to a distal end of said stem section, said distal tip section including, on an end, a small opening, said small opening comprising an elastic restrictor that, when operable, changes in size in response to a change in fluid flow through said catheter assembly to provide a variable amount of fluid force restriction as fluid flows through said elastic restrictor, such that forces resulting from fluid flow out of said openings in said stem section and from fluid flow out of said elastic restrictor are substantially balanced in both axial and radial directions with respect to said longitudinal axis of said portion of said stem section containing said sidewall.

4. The catheter assembly of claim 3, wherein said openings of said stem section are holes.

5. The catheter assembly of claim 3, wherein said at least one of said openings of said stem section causes at least some fluid exiting an internal lumen of said catheter assembly to flow in a retrograde direction to a fluid stream.

6. The catheter assembly of claim 3, wherein said openings of said stem section and said small opening of said distal tip section are configured to provide a cumulative, substantially zero fluid-force vector in all directions.

7. The catheter assembly of claim 3, wherein said catheter assembly has a maximum external diameter of about 4 French.

8. The catheter of claim 1, wherein said elastic restrictor, when operable, increases in size in response to an increase in fluid flow through said tubular structure.

9. The catheter assembly of claim 3, wherein said elastic restrictor, when operable, increases in size in response to an increase in fluid flow through said catheter assembly.

10. The catheter of claim 1, wherein said openings are arranged such that forces resulting from fluid flow out of said openings and out of said elastic restrictor result in a substantially net fluid force of zero.

11. The catheter assembly of claim 3, wherein forces resulting from fluid flow out of said openings in said stem section and out of said small opening of said distal tip section result in a substantially net fluid force of zero.

12. The catheter of claim 1, wherein said elastic restrictor is not included on said sidewall of said distal end of said tubular structure.

13. The catheter of claim 1, wherein said tubular structure enables fluid flow rates in a range of approximately 0 to 40 ml/sec without failure of said tubular structure.

14. The catheter assembly of claim 3, wherein said elastic restrictor is not formed in said sidewall of said stem section.

15. The catheter of claim 1, wherein said elastic restrictor is formed along said longitudinal axis of said distal end of said tubular structure that contains said sidewall on which said openings are formed.

16. The catheter assembly of claim 3, wherein said elastic restrictor is formed along said longitudinal axis of said portion of said stem section that contains said sidewall on which said one or more openings are formed.

17. The catheter of claim 1, wherein with respect to said longitudinal axis of said distal end of said tubular structure that contains said sidewall on which said openings are formed, at least one axial force vector component resulting from fluid flow out of said at least one angled opening is substantially balanced by an axial force vector component resulting from fluid flow out of said elastic restrictor.

18. The catheter assembly of claim 3, wherein with respect to said longitudinal axis of said portion of said stem section containing said sidewall on which said one or more openings are formed, at least one axial force vector component resulting from fluid flow out of said at least one angled opening is substantially balanced by an axial force vector component resulting from fluid flow out of said elastic restrictor.

* * * * *